United States Patent
Saito et al.

(10) Patent No.: US 8,040,772 B2
(45) Date of Patent: Oct. 18, 2011

(54) METHOD AND APPARATUS FOR INSPECTING A PATTERN SHAPE

(75) Inventors: Keiya Saito, Hiratsuka (JP); Takenori Hirose, Yokohama (JP); Hideaki Sasazawa, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 389 days.

(21) Appl. No.: 12/425,438

(22) Filed: Apr. 17, 2009

(65) Prior Publication Data

US 2009/0262621 A1    Oct. 22, 2009

(30) Foreign Application Priority Data

Apr. 18, 2008 (JP) ................................. 2008-108875

(51) Int. Cl.
   *G11B 7/00*     (2006.01)
   *G01N 21/00*    (2006.01)
(52) U.S. Cl. ............... 369/53.1; 369/53.15; 356/237.3
(58) Field of Classification Search .... 369/53.15–53.17, 369/53.1–53.13, 53.42; 356/237.1–237.5
   See application file for complete search history.

(56) References Cited

U.S. PATENT DOCUMENTS

| | | | | |
|---|---|---|---|---|
| 4,180,830 | A * | 12/1979 | Roach | 369/53.41 |
| 5,774,222 | A * | 6/1998 | Maeda et al. | 356/394 |
| 6,512,578 | B1 * | 1/2003 | Komatsu et al. | 356/237.5 |
| 6,621,568 | B1 * | 9/2003 | Yonezawa | 356/237.2 |
| 6,903,888 | B2 * | 6/2005 | Leigh et al. | 369/53.1 |
| 7,623,427 | B2 * | 11/2009 | Jann et al. | 369/53.15 |
| 7,672,799 | B2 * | 3/2010 | Shimura et al. | 356/237.2 |
| 2003/0011760 | A1 | 1/2003 | Vaez-Iravani et al. | |
| 2003/0178588 | A1 * | 9/2003 | Ota | 250/559.45 |
| 2004/0246476 | A1 | 12/2004 | Bevis et al. | |
| 2007/0046931 | A1 * | 3/2007 | Oomori et al. | 356/237.2 |
| 2007/0076195 | A1 * | 4/2007 | Yamaguchi et al. | 356/237.1 |
| 2008/0291436 | A1 * | 11/2008 | Aiko et al. | 356/237.2 |
| 2009/0002695 | A1 | 1/2009 | Saito et al. | |

FOREIGN PATENT DOCUMENTS

| | | |
|---|---|---|
| JP | 2003-149159 | 5/2003 |
| JP | 2007-526444 | 9/2007 |
| JP | 2007-304062 | 11/2007 |
| JP | 2009-004610 | 1/2009 |
| WO | WO 2004/111623 A1 | 12/2004 |

OTHER PUBLICATIONS

Yang et al., "Line-profile and critical dimension correlation between a normal incidence optical CD metrology system and SEM", Proc. SPIE vol. 4689, 2002, pp. 966-976.

\* cited by examiner

*Primary Examiner* — Thang Tran
(74) *Attorney, Agent, or Firm* — Antonelli, Terry, Stout & Kraus, LLP.

(57) ABSTRACT

An apparatus for inspecting a pattern shape of a magnetic record medium or its stamper includes: a moving mechanism, on which an object to be inspected where a pattern is formed is placed and which moves the object to be inspected in a radial direction while rotating the object; an irradiating optical system that applies illuminating light of a wide band including far ultraviolet light to the object to be inspected moved in the radial direction while rotating the object by the moving mechanism in a polarized state suitable for the object to be inspected from an oblique direction; a detecting optical system that detects zero-order reflected light generated from the object to be inspected irradiated by the irradiating optical system; and a shape inspection unit that inspects a pattern shape formed on the object to be inspected based on a spectral reflectance waveform obtained by dispersing the detected zero-order reflected light, thereby inspecting the pattern shape at a high speed and with high sensitivity.

17 Claims, 12 Drawing Sheets

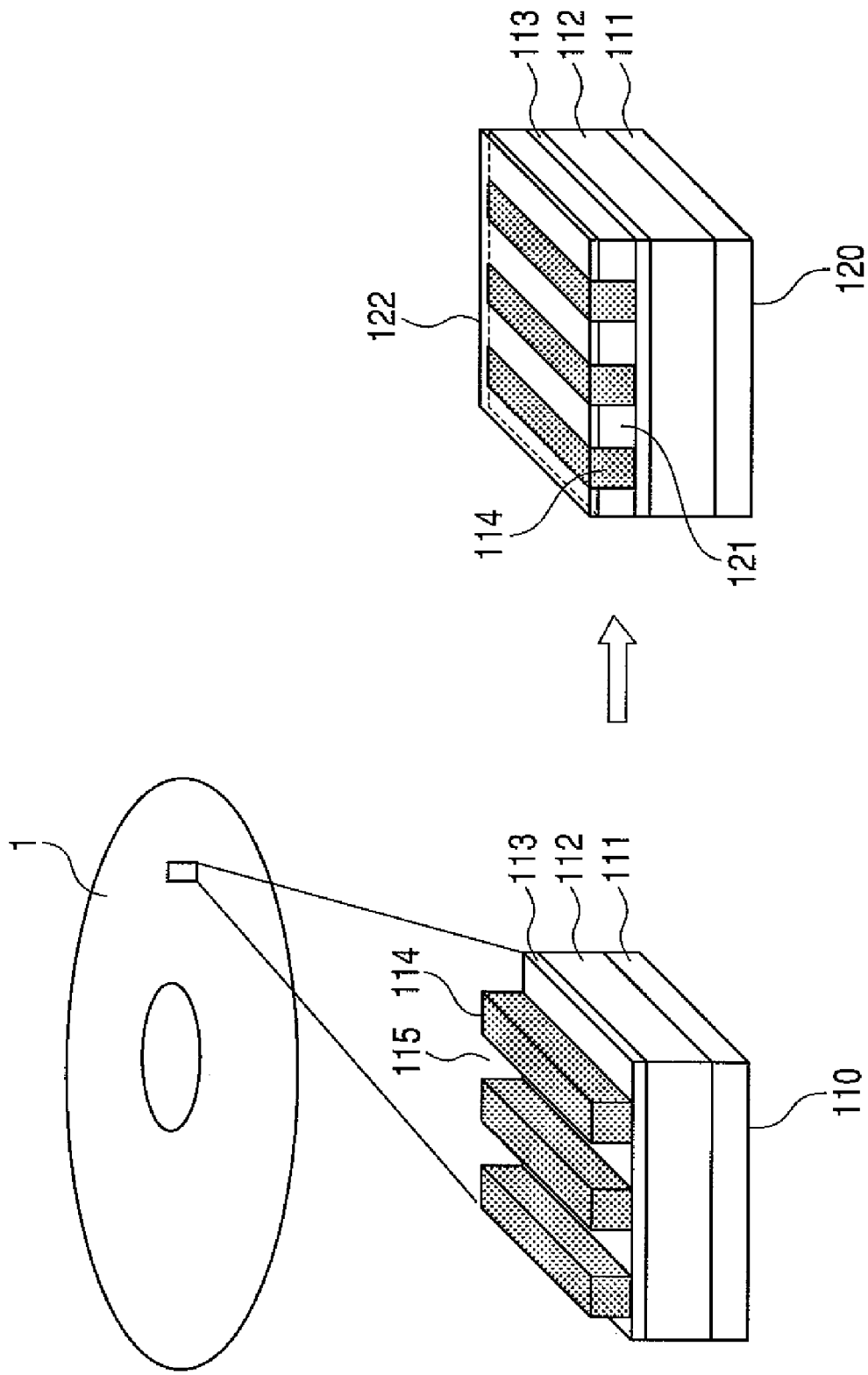

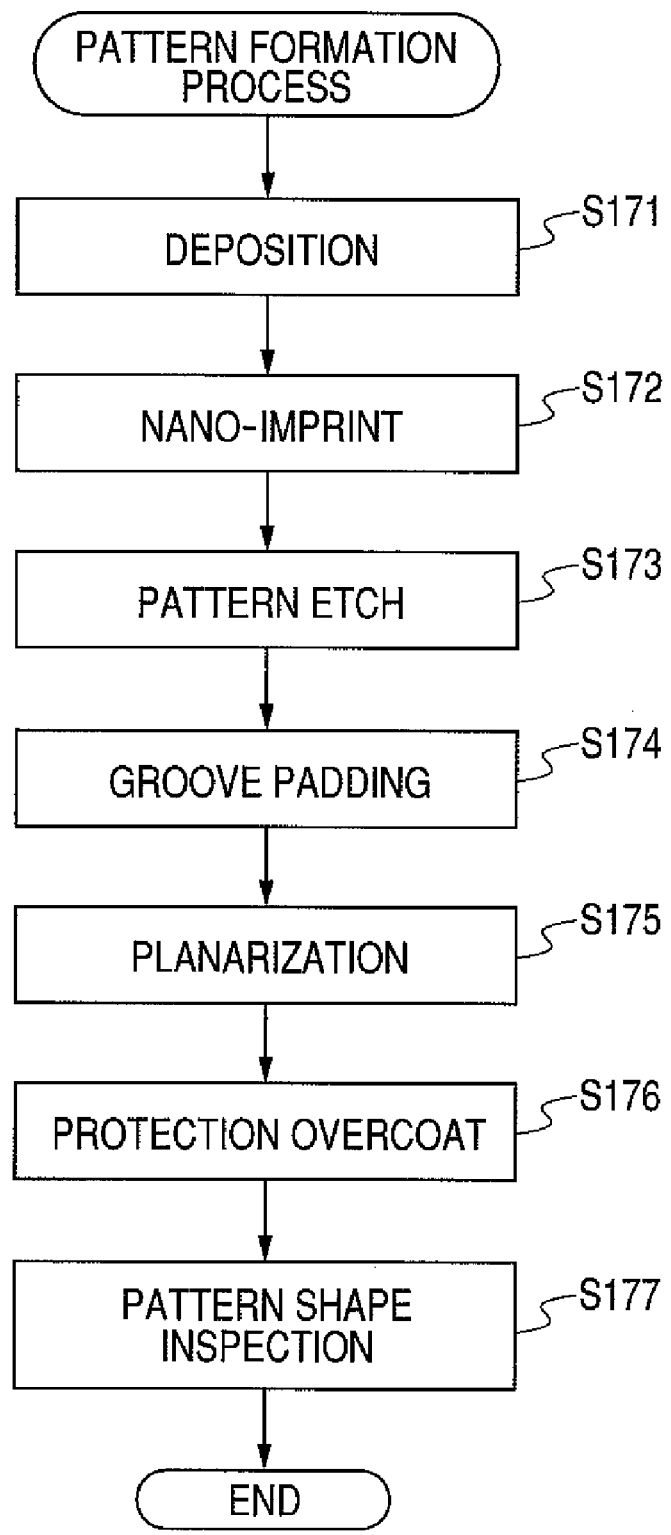

METHOD AND APPARATUS FOR INSPECTING A PATTERN SHAPE

CLAIM OF PRIORITY

The present application claims priority from Japanese Patent Application JP 2008-108875 filed on Apr. 18, 2008, the content of which is hereby incorporated by reference into this application.

BACKGROUND OF THE INVENTION

This invention relates to an apparatus for inspecting a pattern shape of a magnetic record medium formed of a patterned medium or a bit patterned medium as an object to be inspected, its stamper or a master as a die of the stumper at high speed and with high sensitivity, and a method thereof.

In recent years, the spread of a mobile device, a digital AV apparatus and so on has been accelerated in addition to a PC and a server, so that the demand toward a hard disc drive (HDD) has been increased, and the quantity of information treated by the HDD has been remarkably increased. On the other hand, miniaturization of the HDD is required to heighten the recording density of the magnetic record media of the HDD. With an increase in recording density of the HDD, vertical magnetic recording system has been developed, but even in the vertical magnetic recording system, with an increase in recording density, the influence due to mutual magnetic interference of adjacent tracks becomes larger, so that it reaches the limitations. Therefore, as a system for recording and reproducing only an object track, development on the discrete track media adapted to physically work a track and magnetically discrete it has been performed. Further, in order to increase the recording density, development on the bit patterned media adapted to record one bit on one magnetic particle has been progressing.

In the discrete track media and the bit patterned media, differently from the conventional magnetic record medium, it is necessary to form the track and the bit pattern. The sizes of the track and the bit pattern are extremely small as much as tens of nanometers, and photo nano-imprint is used as a method of manufacturing a micro-pattern at a low cost.

Then, when variation in size and shape of a pattern, a defect or short-circuit is caused in a pattern formed by the photo nano-imprint technology, the magnetic record medium does not normally operate, and it becomes sometimes defective. Therefore, it is necessary to inspect whether or not a pattern shape is suitable formed. When a defect is found in a stamper serving as a die of the pattern, the defect is copied. Therefore, higher-accuracy inspection is needed. Although SEM (Scanning Electron Microscope) and AFM (Atomic Force Microscope) are cited as a system for inspecting a defect of a micro-pattern, they cannot be applied to inline inspection from a viewpoint of throughput. On the other hand, as a device for detecting a pattern shape defect with high throughput, an optical surface inspection device and an optical critical dimension (OCD) measuring device are cited.

The conventional surface inspection device and OCD measuring device are known in JP-A-2007-304062, JP-T-2007-526444, JP-A-2003-149159 and "Line-profile and critical dimension correlation between a normal incidence optical CD metrology system and SEM", Proc. SPIE Vol. 4689, 2002, pp 966-976.

In JP-A-2007-304062, it is described that polarized light is applied obliquely to a periodic step pattern on a semiconductor wafer, in reflection, orthogonal polarized light is detected, and the linearity of the periodic step pattern is detected from the intensity of detected light to determine the quality of a focus and the light exposure in exposing a resist pattern.

JP-T-2007-526444 describes an inspection system including an illuminating system, which illuminates a specimen, a condenser configured to condense light scatted from the specimen, a segmented detector, which individually detects different parts of the light to store azimuth and polar angle information on the different parts of the light and generates signals representing the different parts of the light, and a processor, which detects a defect on the specimen from the signal.

JP-A-2003-149159 describes a system for inspecting the surface of a specimen such as a semiconductor wafer, including an illuminating system, which directs a first light beam at a slant incidence angle to the surface of a specimen and directs a second light beam at a substantially vertical angle to the surface of the specimen, a collecting system, which collects at least some of the first and second light beams returning from the surface of the specimen, and a detecting system, which processes the collected parts of the first and second light beams.

"Line-profile and critical dimension correlation between a normal incidence optical CD metrology system and SEM", Proc. SPIE Vol. 4689, 2002, pp 966-976 describes measurement for CD (Critical Dimension) of a recessed and projecting pattern of a resist film on the poly-Si in the Si substrate by applying scatterometory having the vertical incidence and vertical detection optical system.

JP-A-2007-304062, however, relates to defect detection using linearity detection, and JP-T-2007-526444 and JP-A-2003-149159 relate to defect detection using detection of scattered light, and the inspection of a pattern shape is not taken into consideration.

"Line-profile and critical dimension correlation between a normal incidence optical CD metrology system and SEM", Proc. SPIE Vol. 4689, 2002, pp 966-976 relates to the technology of measuring CD (Critical Dimension) of a recessed and projecting pattern of a resist film on poly-Si in a Si substrate by applying scatterometory having the vertical incidence and vertical detection optical system, and the inspection of a pattern shape at high speed and with high sensitivity concerning a recessed and projecting pattern of a magnetic record medium such as a patterned medium or a bit patterned medium and a recessed and projecting pattern of a stamper in forming the recessed and projecting pattern of the magnetic record medium by nano-imprint is not taken into consideration.

SUMMARY OF THE INVENTION

The present invention relates to apparatus and method for inspecting a pattern shape, which may inspect, at a high speed and with high sensitivity, a pattern shape of a magnetic record medium formed of a patterned medium or a bid patterned medium, its stamper or a master as a die of the stamper as an object to be inspected.

That is, the invention provides an apparatus including: a moving mechanism on which an object to be inspected where a pattern is formed is placed and which moves the object to be inspected in the radial direction while rotating the object; an irradiating optical system that applies illuminating light of a wide band including far ultraviolet light to the object to be inspected moved in the radial direction while rotating the object by the moving mechanism in a polarized state suitable for the object to be inspected from an oblique direction; a detecting optical system that detects zero-order reflected light generated from the object to be inspected irradiated by the irradiating optical system; and a shape inspection unit that inspects a pattern shape formed on the object to be inspected based on a spectral reflectance waveform obtained by dispersing the detected zero-order reflected light, and a method thereof.

According to the invention, the inspection can be performed with high throughput for a magnetic record medium formed of a discrete track medium or a bit patterned medium, its stamper or a master as a die of the stamper by detecting the pattern shape at high speed and with high sensitivity regardless of material quality of an object to be inspected.

These and other objects, features and advantages of the invention will be apparent from the following more particular description of preferred embodiments of the invention, as illustrated in the accompanying drawings.

BRIEF DESCRIPTION OF THE DRAWINGS

FIG. 9 is a perspective view showing the case where an object to be inspected is a discrete track medium after groove embedding;

FIG. 10 is a flowchart showing the pattern formation process of a discrete track medium;

DESCRIPTION OF THE PREFERRED EMBODIMENTS

An apparatus and method for inspecting a pattern shape according to the embodiments of the invention will now be described in detail using the drawings.

Embodiment 1

A method and apparatus for inspecting a pattern shape according to a first embodiment of the invention will now be described in detail using FIGS. 1 to 6.

Figure 1:
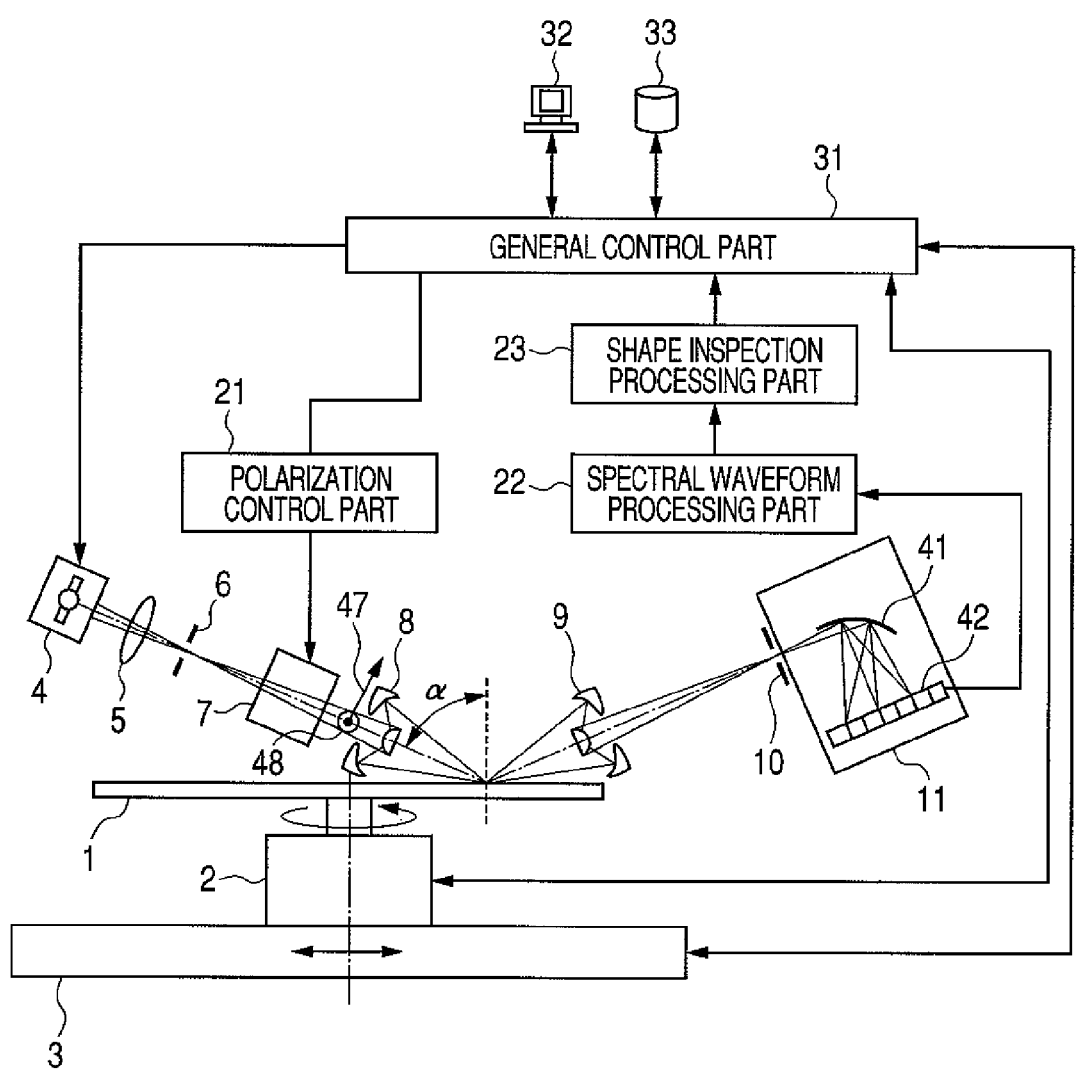
FIG. 1 is a schematic block diagram showing a first embodiment of a pattern shape inspection apparatus.
Figure 2:
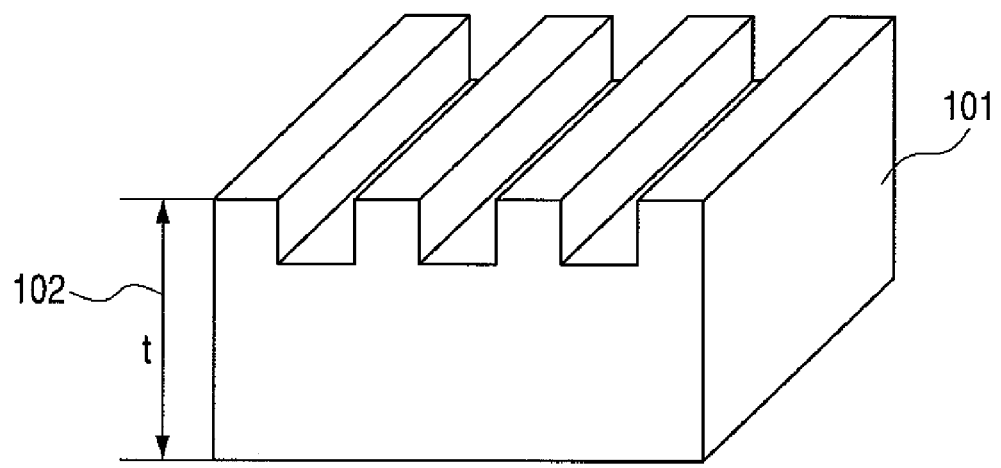
FIG. 2 is a perspective view showing a local structure in the case where an object to be inspected is a quartz stamper to an enlarged scale.

FIG. 1 is a block diagram showing a first embodiment of a pattern shape inspecting apparatus according to the invention. The pattern shape inspection apparatus of the invention inspects a pattern shape of a recessed and projecting pattern in a magnetic film on a magnetic record medium, a recessed and projecting pattern in a stamper, or a recessed and projecting pattern in a master as a die of the stamper, taking a patterned medium of a magnetic storage medium, a stamper in forming the patterned medium by nano-imprint, and a master as a die of the damper as an object to be inspected. FIG. 2 shows an object to be inspected, which is a quartz-made stamper 101 for a discrete track medium.

The pattern shape inspection apparatus of the invention includes: a moving mechanism having a θ stage 2 loaded with a specimen 1 such as a stamper 101 as an object to be inspected, and rotated, and an X stage 3 for moving the θ stage 2 in one direction, on which the object to be inspected is placed, and which moves the object to be inspected in the radial direction while rotating the object; an irradiating optical system having a wide band light source 4 for emitting illuminating light of a wide band including far ultraviolet light (DUV), a condenser lens 5, which condenses the illuminating light, a field stop 6 which determines a detecting visual field on the specimen, a crystal polarizer (a polarizing optical element) 7, which polarizes the illuminating light in a specified direction to be suitable for the specimen as the object to be inspected, an illuminating lens 8, which images the illuminating light polarized in a specified direction on the specimen 1 from the oblique direction, and a polarization control part 21, which controls the rotation of the crystal polarizer 7; a detecting system having an objective lens 9, which images zero-order reflected light from the specimen 1 as the object to be inspected and a diaphragm 10, which shields stray light and the like; a spectroscope 11 having a diffraction grating 41 for dispersing detected light (zero-order reflected light) and a linear photo-detector 42, which detects spectral waveform dispersed by the diffraction grating 41; a shape inspection unit having a spectral waveform processing part for inputting the spectral waveform detected by the spectroscope 11, and A/D converting the same to obtain the digitized spectral reflectance waveform and a shape inspection processing part 23 for inspecting the pattern shape of the inspection object based on the spectral reflectance waveform obtained by the spectral waveform processing part 22; a general control part 31 for controlling the whole sequence; and an input/output terminal 32 and a database 33, which are connected to the general control part 31.

In order to inspect a pattern shape of a recessed and projecting pattern in a magnetic film on the magnetic record medium and a recessed and projecting pattern in a stamper, a change amount in spectral reflectance of the reflected light due to a pattern shape change should be large, and the shape change detecting sensitivity should be high. Therefore, the illuminating light controlled so that the polarization direction is suitable for the object to be inspected is caused to enter the specimen 1 obliquely, and the zero-order reflected light (regular reflection light) from the specimen 1 is detected from the oblique direction. Even when the object to be inspected is a quartz-made stamper transmitting UV light including DUV light, the illuminating light is caused to enter obliquely, whereby the reflectance is enhanced, and the quantity of detected light is increased to inspect the pattern shape with high sensitivity.

The operation of the pattern shape inspection apparatus in accordance with the invention will now be described. The specimen 1 is held on the θ stage 2, and rotated, and it is moved in one direction by the X stage 3. The rotating position of the θ stage 2 and the moving position of the X stage 3 are input to the general control part 31. The wide band light source 4 emits illuminating light (wavelength is 200 to 800 nm, for example) of a wide band (multi-wavelength) including far ultraviolet (DUV) light, and the light source is constructed by a Xenon lamp, a halogen lamp, a heavy hydrogen lamp or a combination thereof. The illumination is slant incidence at an incident angle α, and the illuminating light is caused to enter substantially at right angles to the radial direction of the specimen 1, that is, the pattern direction of the discrete track.

The illuminating light from the wide band light source 4 is condensed on the field stop 6 by the condenser lens 5. An image of the field stop 6 is formed on the specimen by the reflection type illuminating lens 8, thereby forming a detecting visual field. At that time, the polarization direction (p-polarized 47, s-polarized 48) of the illuminating light is selected and set by the rotation control to the crystal polarizer 7 from the polarization control part 21 to be suitable for the kind of the object to be inspected. As mentioned later, the polarization direction of the illuminating light is previously obtained from the conditions for measuring the pattern shape of the specimen 1 with high sensitivity, and stored in the database 33, whereby the polarization direction of the illuminating light is selected and set to be suitable for the kind of the object to be inspected. Supposing that the field stop 6 is a square having equal longitudinal and horizontal dimensions, the slant incidence makes a square of a detection visual field on the specimen 1, whose dimensions are 1/cos α times longer in the optical axis direction. The shape of the field stop 6 is determined in consideration of this point.

The zero-order reflected light (regular reflection light) from the pattern of the specimen 1 is condensed by the objective lens 9, and imaged on the diaphragm 10. In this case, the illuminating lens 8 and the objective lens 9 use a reflection type lens having a small absorption loss of the lens and capable of reducing chromatic aberration in a far ultraviolet light (DUV) region of the illuminating light. The diaphragm 10 is sized corresponding to the size of the detecting visual field on the specimen 1, so that it shields stray light and light not imaged on the diaphragm 10. For example, some of the incident light on the specimen 1 is transmitted through the surface of the specimen 1 and reflected on the back of the specimen 1 to again reach the surface of the specimen 1, and then emitted parallel to the zero-order reflected light from the surface of the specimen 1.

As shown in FIG. 2, when the thickness 102 of the specimen 1 is t, and the incident angle α is 70°, the exit position from the surface of the specimen 1 is at a distance of 1.68 t from the incident position, which is larger than the size (about 100 μm at a maximum) in the radial direction of the detecting visual field, so that the reflected light from the back of the specimen 1 can be shielded by the diaphragm 10. The zero-order reflected light (regular reflection light) from the detecting visual field is transmitted through the diaphragm 10 to reach the spectroscope 11. In the spectroscope 11, the detecting light (zero-order reflected light) transmitted through the diaphragm 10 is dispersed by the diffraction grating 41, and the spectral waveform is detected using the linear photo detector 42. The spectral waveform detected by the linear photo detector 42 is input to the spectral waveform processing part 22, and A/D converted in the spectral waveform processing part 22 to obtain a digitized spectral reflectance waveform. Subsequently, the shape inspection processing part 23 inspects the shape of a recessed and projecting pattern of the object to be inspected from the spectral reflectance waveform obtained by the spectral waveform processing part 22.

Figure 3:
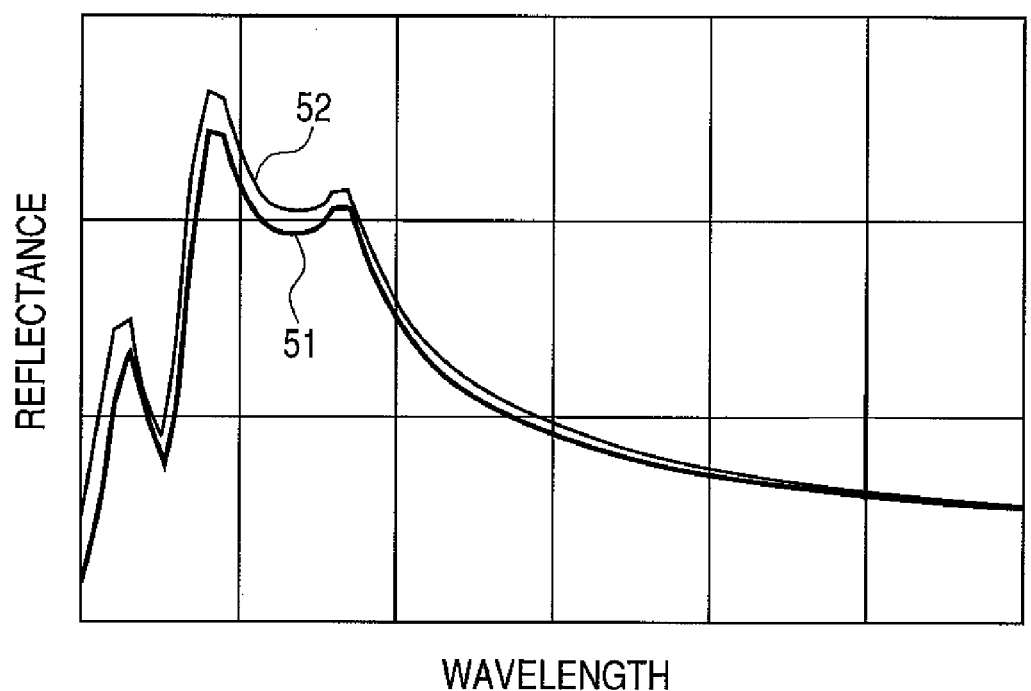
FIG. 3 is a diagram for explaining the relationship between the spectral reflectance waveform of an object to be inspected obtained from an actual object to be inspected and a reference spectral reflectance waveform obtained from a normal pattern (a standard pattern)

There are some methods for shape inspection for the recessed and projecting pattern. According to a first method, as shown in FIG. 3, a reference spectral reflectance waveform 51 is previously detected from a standard specimen (a pattern shape is a known standard specimen) having a normal recessed and projecting pattern, or calculated using an electromagnetic wave analysis technique such as RCWA (Rigorous Coupled-Wave Analysis) and stored in the database 33, and the shape inspection processing part 23 calculates a mean error concerning a wavelength (e.g. a mean square error concerning a wavelength) between a spectral reflectance waveform 52 of an object to be inspected, which is detected from a specimen 1 of an actual object to be inspected, and the reference spectral reflectance waveform 51, and determines to be abnormal in the recessed and projecting pattern shape of the actual object to be inspected (to be not formed according to the specified dimensions (design dimensions) when the calculated value is more than a threshold. Thus, the inspection is performed.

According to a second method, previously various reference spectral reflectance waveforms are obtained from the reference spectral reflectance waveform 51 detected from a standard specimen having a normal recessed and projecting pattern when various recessed and projecting pattern shapes change using an electromagnetic wave analysis technique such as RCWA to generate a library in a database 33, and the shape inspection processing part 23 compares a spectral reflectance waveform 52 of an object to be inspected, which is detected from a specimen 1 of an actual object to be inspected, with the above various reference spectral reflectance waveforms on the library to measure a recessed and projecting pattern shape of the actual object to be inspected from the matching reference spectral reflectance waveform, and determines whether or not the measured recessed and projecting pattern shape is abnormal. Thus, the inspection is performed.

According to a third method, the shape inspection processing part 23 calculates various reference spectral reflectance waveforms in the case of changing the shape of a recessed and projecting pattern to a spectral reflectance waveform 52 detected from a specimen 1 of an actual object to be inspected using an electromagnetic wave analysis technique such as RCWA, measures the recessed and projecting pattern shape itself of the actual object to be inspected by fitting the calculated various reference spectral reflectance waveforms to the spectral reflectance waveform 52 of the object to be inspected, which is detected from the specimen 1 of the actual object to be inspected, and determines whether or not the measured recessed and projecting pattern shape is abnormal. Thus, the inspection is performed.

Figure 4:
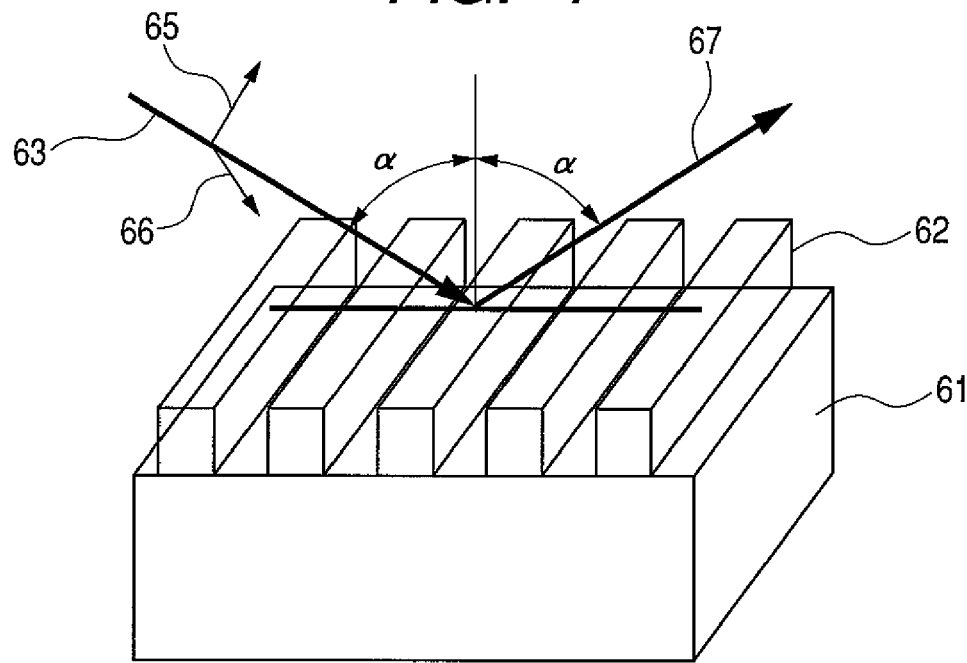
FIG. 4 is a diagram for showing a local optical model for simulation in the case where an object to be inspected is a quartz stamper to an enlarged scale.
Figure 5:
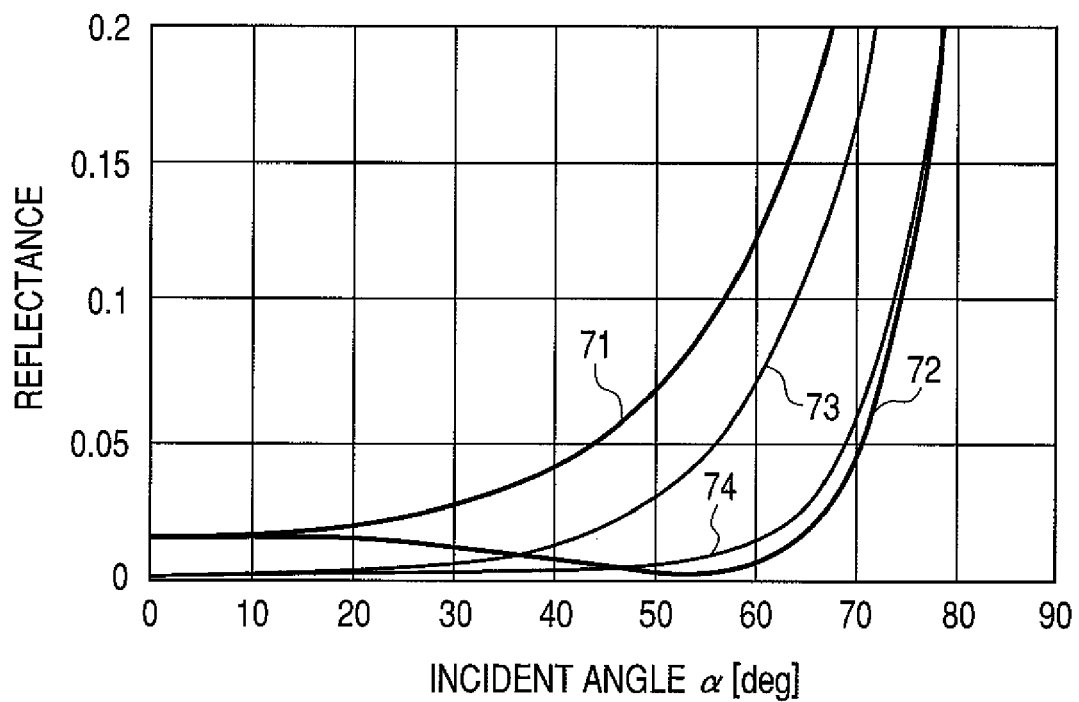
FIG. 5 is a diagram showing the reflectance dependency on an incident angle α obtained by simulation in the case where the object to be inspected is a quartz stamper.

The relationship between the polarization direction of illuminating light and the detecting sensitivity of a pattern shape in accordance with the first embodiment of the invention will now be described. A simulation is, as shown in FIG. 4, performed so that the illuminating light 63 of a wide band including DUV light is applied to a recessed and projecting pattern 62 on a substrate 61 with an incident angle α and the polarization direction (p-polarized light 65 and s-polarized light 66) varied, from the right-angled direction to the pattern direction, to detect the spectral waveform of reflected light 67, thereby obtaining a reference spectral reflectance waveform of a standard recessed and projecting pattern and a spectral reflectance waveform of an object to be inspected in the case where the recessed and projecting pattern changes from the standard recessed and projecting pattern in shape such as width, height and side wall angle. FIG. 5 shows the reflectance dependency on the incident angle α of the reflected light in a standard pattern in the case where a specimen 1 is quartz (that is, the substrate 61 and the pattern 62 are quartz). When any recessed and projecting pattern is not provided on the substrate 61, the reflectance dependency on the substantially same incident angle α is shown regardless of wavelength λ1, λ2 (λ2<0.4 μm<λ1), but when a recessed and projecting pattern 62 is provided thereon, the reflectance dependency 72 on the incident angle α of p-polarized light with the wavelength λ1, the reflectance dependency 74 on the incident angle α of p-polarized light with the wavelength λ2, the reflectance dependency 71 on the incident angle α of s-polarized light with the wavelength λ1 and the reflectance dependency 73 on the incident light α of s-polarized light with the wavelength λ2 are different from one another. In the p-polarized light, the reflectance does not come to zero at an angle equivalent to a Brewster angle. However, both in the p-polarized light and in the s-polarized light, the reflectance is small at an incident angle α=0° (vertical incidence), and in the s-polarized light, as the incident angle α becomes larger, the reflectance becomes larger. This is similar to a tendency in the case where any recessed and projecting pattern is not provided. Therefore, the quantity of detection light detected by the spectroscope 11 can be increased by enlarging the incident angle α at which the illuminating light of a wide band including DUV light enters the specimen.

Figure 6A:
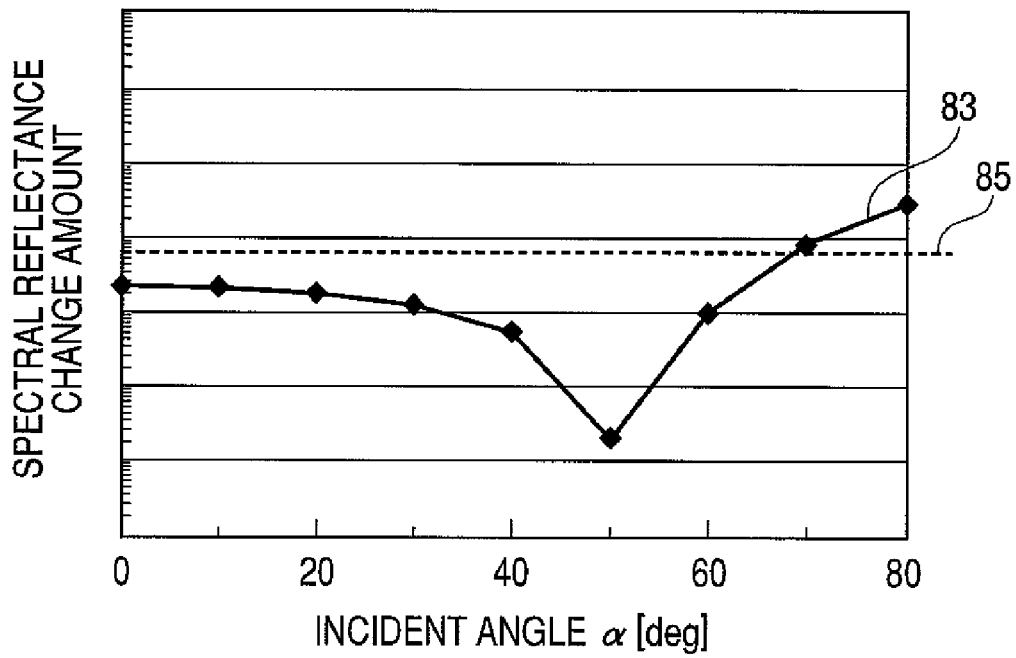
FIG. 6A is a diagram showing the spectral reflectance change amount to the incident angle α obtained by simulation according to the polarization direction in the case where the object to be inspected is a quartz stamper, which is the first embodiment, and showing the case of using p-polarized light as incident light.
Figure 6B:
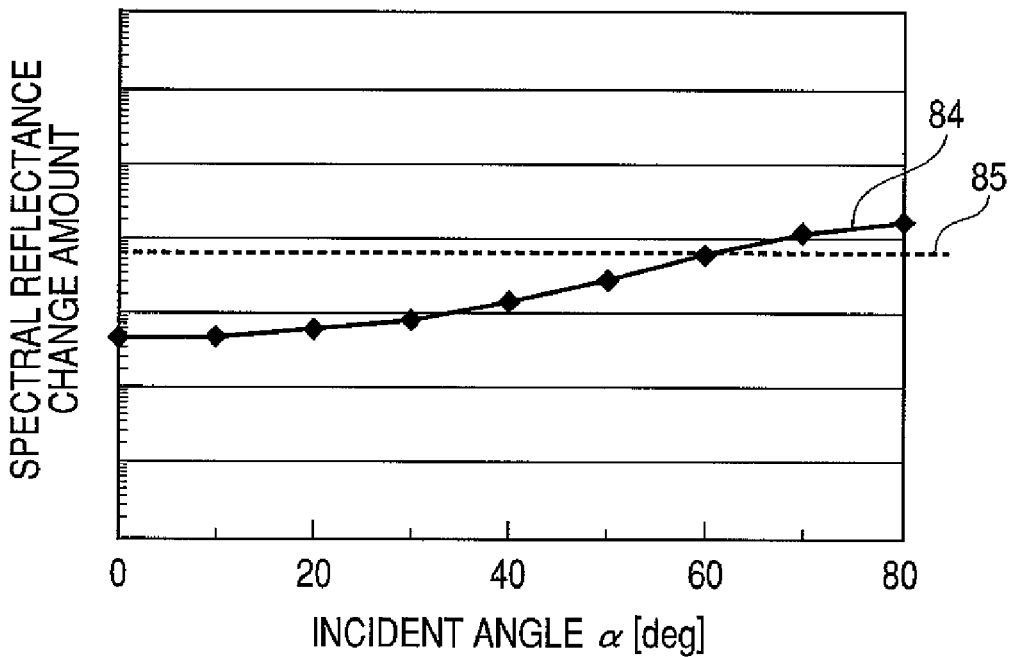
FIG. 6B shows the case of using s-polarized light as incident light.

The change in spectral reflectance waveform when the shape of the recessed and projecting pattern of the object to be inspected in accordance with the invention changes from the standard recessed and projecting pattern will now be described using FIGS. 6A and 6B. FIGS. 6A and 6B show the case where the recessed and projecting pattern changes in width among the width, height and side wall angle. Also in the other cases of the height and the side wall angle, the similar tendency is shown. The change of the spectral reflectance waveform is, as shown in FIG. 3, calculated by a means error (e.g. a mean square error) concerning a wavelength between a reference spectral reflectance waveform 51 detected from a normal standard recessed and projecting pattern and a spectral reflectance waveform 52 of an object to be inspected, which is detected when the standard recessed and projecting pattern is changed in pattern width, and this is defined as a spectral reflectance change amount. FIG. 6A shows a spectral reflectance change amount 83 at each incident angle in the case of the p-polarized light when the incident angle α [deg] is changed, and FIG. 6B shows a spectral reflectance change amount 84 at each incident angle in the case of the s-polarized light when the incident angle α [deg] is changed.

As shown in FIG. 6A, in the case of the p-polarized light, the spectral reflectance change amount 83 decreases near an incident angle 50°, and again increases as the incident angle increases. As shown in FIG. 6B, in the case of the s-polarized light, the spectral reflectance change amount 84 uniformly increases to an increase in incident angle. When FIG. 6A and FIG. 6B are compared with each other, the spectral reflectance change amount is larger in the s-polarized light than in the p-polarized light near 70°. When the S/N of the linear photo detector 42 of the spectroscope 11 shown in FIG. 1 is taken into consideration, a threshold 85 of detectable spectral waveform reflectance change amount is as shown in FIGS. 6A and 6B. Although the level of threshold 85 is highly probably lowered by noise reduction and high sensitivity of the linear photo detector 42, highly probably a change in the recessed and projecting pattern shape can be detected with high sensitivity as a change in spectral reflectance waveform by s-polarized light illumination near an incident angle 70°. When the object to be inspected is a quartz stamper 101, in the pattern shape inspection apparatus as shown in FIG. 1, it is desirable that the incident angle α is 70° or more, and the polarization direction is s-polarized light 48.

The shape inspection processing part 23 determines to be shape abnormality (shape defect) when the spectral reflectance change amount is a threshold of 85 or more, records the shape abnormal position in the database 33, and displays it on the input/output terminal 32.

As described above, when the object to be inspected is the quartz stamper 101, s-polarized light is selected by slant incidence (an incident angle α is 70° or more) as the illuminating light of a wide band including DUV light, and the spectral reflectance waveform of zero-order reflected light (regular reflection light) is detected as the detected waveform, whereby a change in the recessed and projecting pattern shape can be detected with high sensitivity.

Second Embodiment

Figure 7:
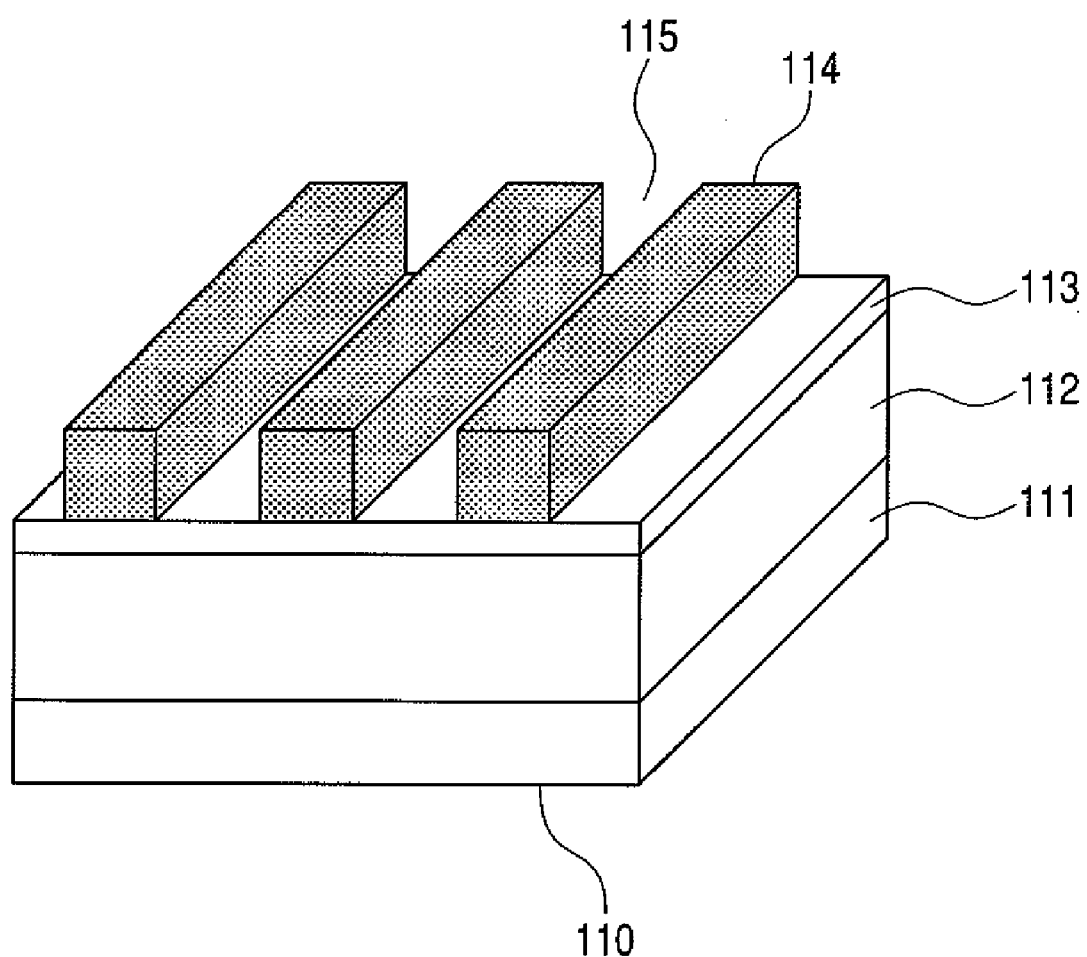
FIG. 7 is a perspective view showing a local structure in the case where an object to be inspected is a discrete track medium to an enlarged scale.

A second embodiment of a pattern shape inspection apparatus according to the invention will now be described using FIG. 1, FIG. 4, FIG. 7 and FIG. 8. This second embodiment is different from the first embodiment in that as a specimen 1, a discrete track medium 110 shown in FIG. 7 is taken as an inspection object instead of the stamper shown in FIG. 2. The discrete track medium 110, as shown in FIG. 7, includes a substrate 111, a soft magnetic ground layer 112, an intermediate layer 113 and a recording layer 114, and a track groove 115 is formed in the recording layer 114 part. In an actual product, after that, the track groove 115 is padded with non-magnetic material, and after planarization, a protective film (not shown) is formed, and a lubricating film (not shown) is formed thereon. Thus, the medium where the recessed and projecting part of the pattern is padded is used, whereby the floating amount of a magnetic head can be stabilized.

In the second embodiment, since the object to be inspected is the discrete track medium 110, it is necessary to attain higher throughput of inspection as compared with the case of the stamper. Therefore, in the linear photo detector 42 of the spectroscope 11, not the array element, but the plurality of photomultiplier elements are disposed parallel to attain high speed. The operations of the respective components in the second embodiment are the same as those of the first embodiment except that the polarization direction of the crystal polarizer 7 is p-polarized light.

The relationship between the polarization direction of illuminating light and the shape detecting sensitivity of a pattern shape in accordance with the second embodiment of the invention will now be described based on the detecting simulation of a spectral waveform similarly to the first embodiment. In the second embodiment, since the object to be inspected is the discrete track medium 110, instead of the substrate 61 shown in FIG. 4, a multi-structure of the substrate 111, the soft magnetic ground layer 112 and the intermediate layer 113 is taken, and instead of the pattern 62 in FIG. 4, the recording layer 114 shown in FIG. 7 is taken, which shows the midway of a manufacturing process. Similarly to the first embodiment, a simulation is, as shown in FIG. 4, performed so that illuminating light 63 of a wide band including DUV light is applied to a recessed and projecting pattern 62 on a substrate 61 with the incident angle α and the polarization direction (p-polarized light 65 and s-polarized light 66) varied from the right-angled direction to the pattern direction, to detect a spectral waveform of reflected light 67, thereby obtaining a reference spectral reflectance waveform of a standard recessed and projecting pattern and a spectral reflectance waveform of an object to be inspected in the case where the recessed and projecting pattern changes from the standard recessed and projecting pattern in shape such as width, height and side wall angle. A mean error (e.g. a mean square error) concerning the wavelength between the obtained reference spectral reflectance waveform and the spectral reflectance waveform of the object to be inspected is calculated to thereby obtain a spectral reflectance waveform change amount in the case where the pattern shape of the object to be inspected changes.

Figure 8A:
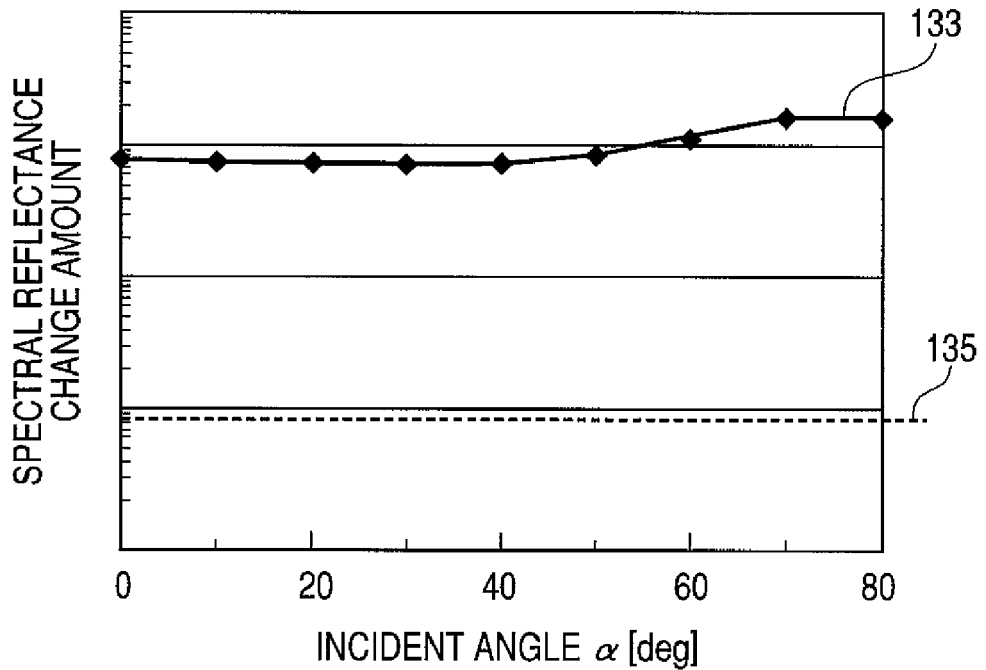
FIG. 8A is a diagram showing the spectral reflectance change amount to the incident angle α obtained by simulation according to the polarization direction in the case where the object to be inspected is a discrete track medium, which is a second embodiment, and showing the case of using p-polarized light as incident light.
Figure 8B:
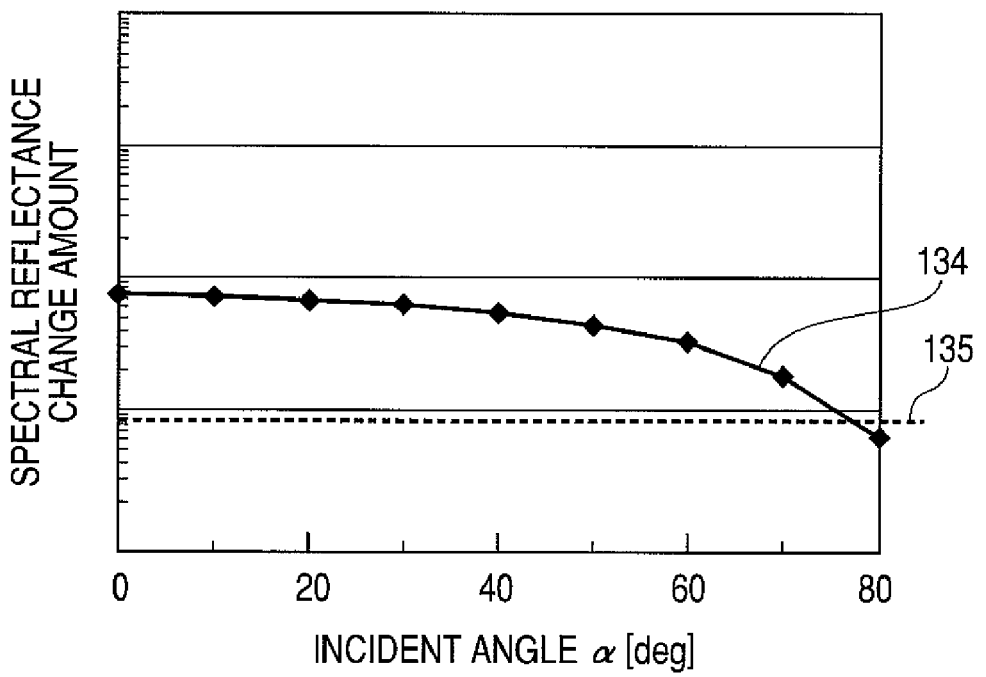
FIG. 8B shows the case of using s-polarized light as incident light.

The simulation results are shown in FIGS. 8A and 8B. FIGS. 8A and 8B show the case where the width of the recording layer 114 changes. FIG. 8A shows a spectral reflectance change amount 133 at each incident angle in the case of p-polarized light when the incident angle α [deg] is changed, and FIG. 8B shows a spectral reflectance change amount 134 at each incident angle in the case of s-polarized light when the incident angle α [deg] is changed.

As shown in FIG. 8A, in the case of the p-polarized light, the spectral reflectance change amount 133 a little decreases near an incident angle 40°, and again increases as the incident angle increases. As shown in FIG. 8B, in the case of the s-polarized light, the spectral reflectance change amount 134 uniformly increases to an increase in incident angle. When FIG. 8A and FIG. 8B are compared with each other, the spectral reflectance change amount is smaller in the s-polarized light, and decreases with an incident angle.

The reason for this is that when a magnetic film is metal, the spectral reflectance is constant regardless of a wavelength in the case of s-polarized light whose polarization direction coincides with the line direction of the pattern. Therefore, it is known that when the incident angle is 70° or more, the spectral reflectance change amount is larger in the p-polarized light than in the s-polarized light, and the sensitivity to a change in the pattern shape is higher. In the second embodiment where the object to be inspected is a discrete track medium, however, the spectral waveform reflectance change amount is larger at almost all incident angles to the threshold 135 of the detectable spectral waveform reflectance change amount in the linear photo detector 42 of the spectroscope 11 even in the case of the p-polarized light shown in FIG. 8A as well as in the case of the s-polarized light shown in FIG. 8B, and the detecting sensitivity is higher as compared with that in the case where the object to be inspected is a quartz stamper.

Even when the object to be inspected is a discrete track medium, the detecting sensitivity changes depending on the material qualities of the pattern 62 and the substrate 61 of the object to be inspected. When the recording layer 114 is made of granular material, for example, the detecting sensitivity is higher in the s-polarized light than in the p-polarized light, and besides, in the case of the s-polarized light, as the incident angle increases, the detecting sensitivity probably becomes higher. In either case, previously the detecting sensitivity depending on the material quality of the object to be inspected is obtained, and the polarization direction is selected according to the material quality, whereby an abnormal change in the recessed and projecting pattern shape can be detected with high sensitivity.

Third Embodiment

A third embodiment of a pattern shape inspection apparatus in accordance with the invention will now be described using FIG. 1 and FIGS. 9 to 12. This third embodiment is different from the second embodiment in that as a specimen 1, a padded discrete track medium 120 in which a track groove 115 is padded with a non-magnetic layer 121, and a protective film 122 is put thereon as shown in FIG. 9, is taken as an inspection object instead of the discrete track medium 110 shown in FIG. 7.

FIG. 10 shows a pattern formation process for a discrete track medium 120. As a method of forming recessed and projecting parts for track grooves, a method of depositing a magnetic film on a substrate and then forming recessed and projecting parts will be described. First, a soft magnetic ground layer 112, an intermediate layer 113, and a recording layer 114 are deposited in order on the substrate 111 (S171). Subsequently, a photo curable resin film is formed on the recording layer 114, and a pattern of a track groove is transferred to the photo curable resin film by nano-imprint (S172). After the pattern is transferred, the photo curable resin layer recessed part and the recording layer 114 are worked by etching to form a track groove 115 in the recording layer 114 (S173). Subsequently, the track groove 115 is padded with a non-magnetic layer 121 (S174), and after planarization (S175), a protective film 122 is formed of DLC (Diamond Like Carbon) or the like (S176). After that, the shape of the pattern is inspected by the pattern shape inspection apparatus in accordance with the third embodiment (S177).

The pattern shape inspection for the discrete track medium 110 in the second embodiment before filling the groove is performed after etching (s173).

Figure 11:
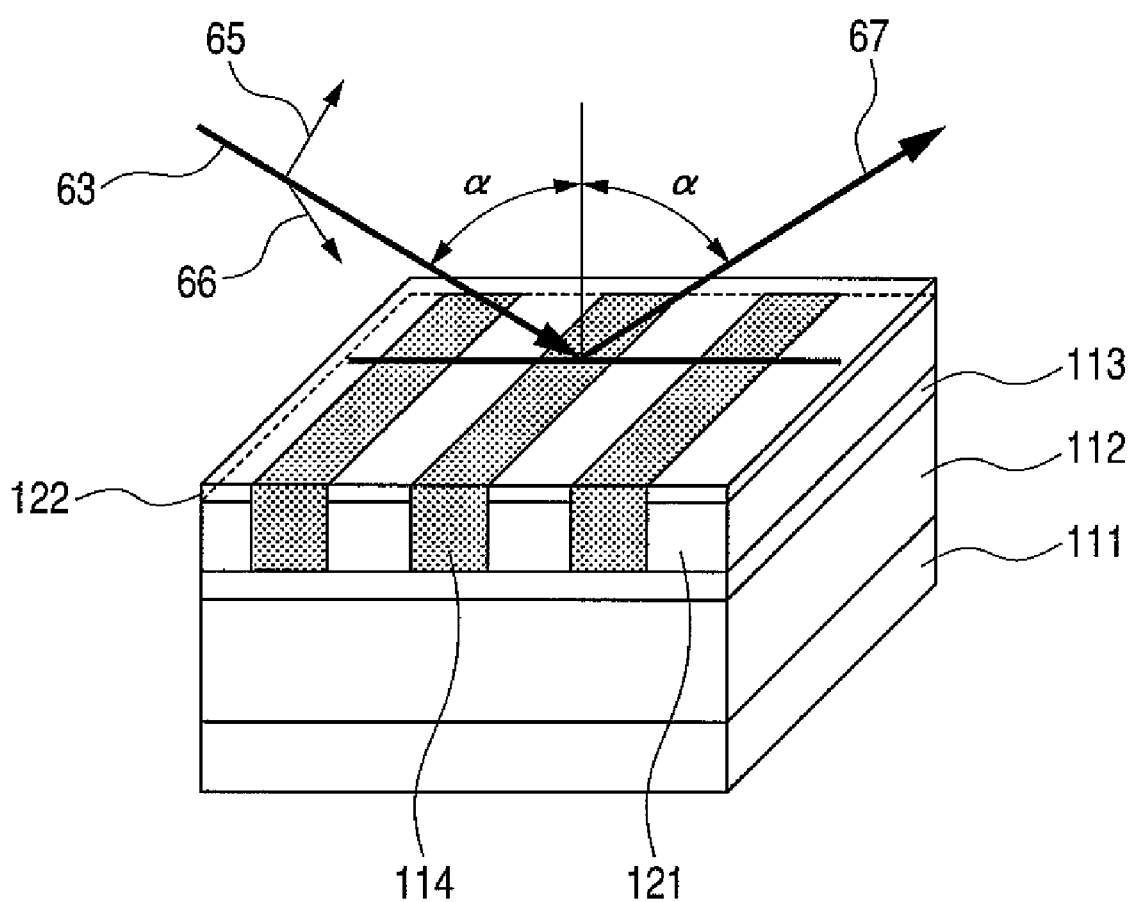
FIG. 11 is a diagram showing a local optical model for simulation in the case where the object to be inspected is the discrete track after groove embedding to an enlarged scale.

Also in the third embodiment, similarly to the second embodiment, a detecting simulation for the spectral waveform is performed. In the third embodiment, as shown in FIG. 11, the simulation is performed so that to a multi-layer structure including the recording layers 114 of the projecting part pattern 62, the groove embedding non-magnetic layer 121 and the protective film 122 in a stacking structure of the substrate 111, the soft magnetic ground layer 112, and the intermediate layer 113, illuminating light 63 of a wide band including DUV light is applied, with the incident angle α and the polarization direction (p-polarized light 65 and s-polarized light 66) varied, thereby detecting the spectral waveform of reflected light 67. A reference spectral reflectance waveform of a standard pattern and a spectral reflectance waveform of an object to be inspected in the case where a pattern changes from the standard pattern in shape such as width, height and side wall angle are obtained, and a mean error (e.g. a mean square error) concerning the wavelength between the obtained reference spectral reflectance waveform and the spectral reflectance waveform of the object to be inspected is calculated to thereby obtain a spectral reflectance waveform change amount in the case where the pattern shape of the object to be inspected changes.

Figure 12A:
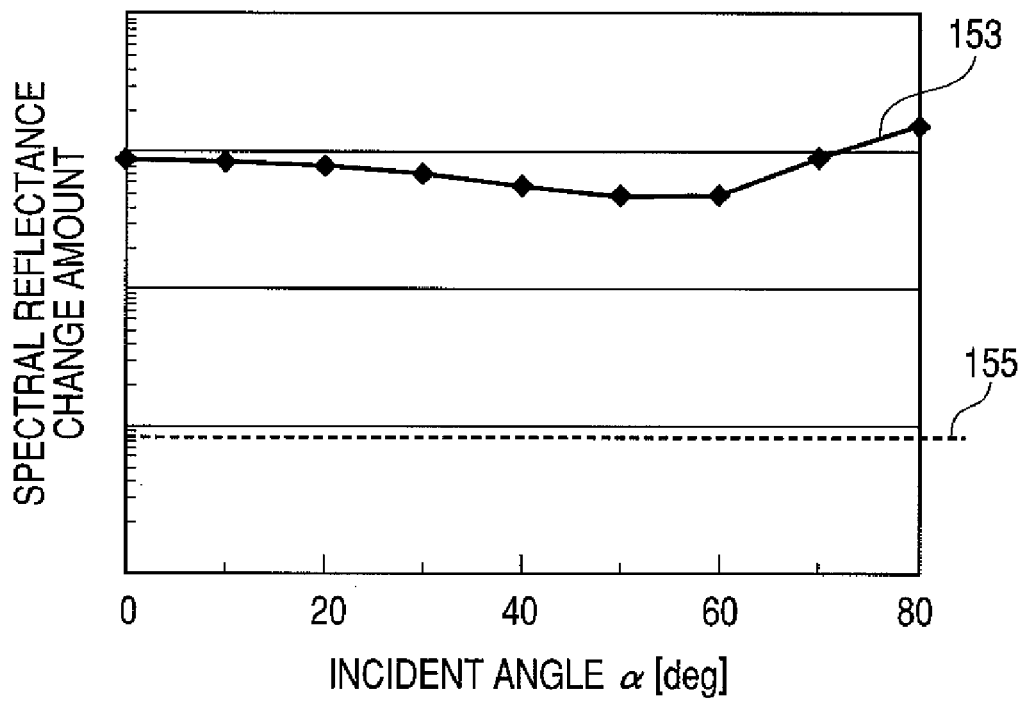
FIG. 12A is a diagram showing the spectral reflectance change amount to the incident angle α obtained by simulation according to the polarization direction in the case where the object to be inspected is a discrete track medium after groove embedding, which is a third embodiment, and showing the case of using p-polarized light as incident light.
Figure 12B:
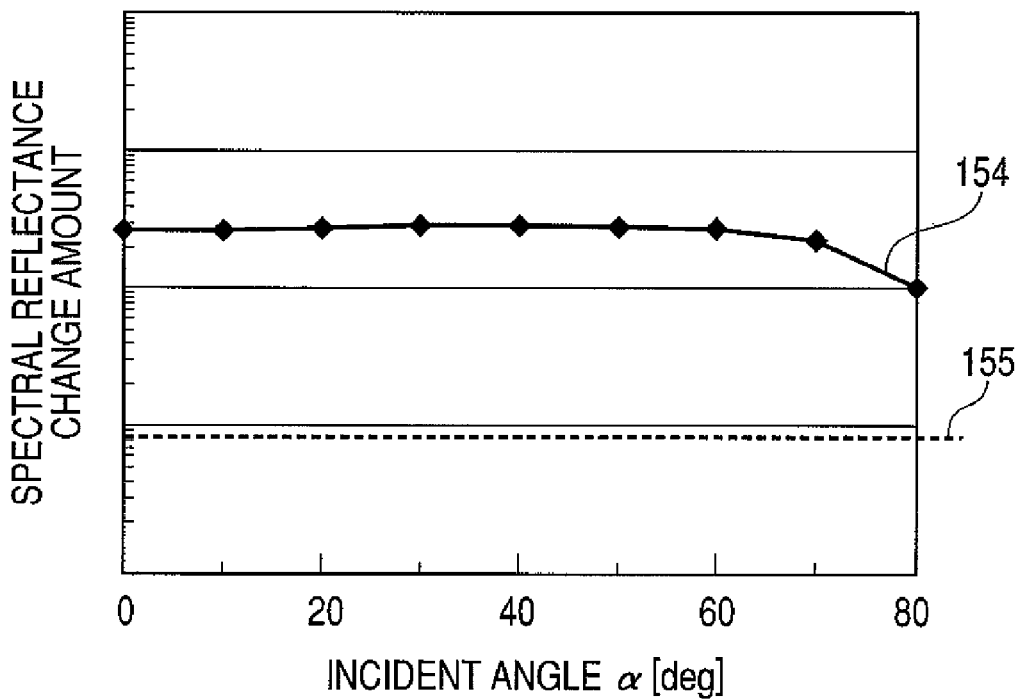
FIG. 12B shows the case of using s-polarized light as incident light.

The simulation results are shown in FIGS. 12A and 12B. FIGS. 12A and 12B show the case where the width of the recording layer 114 changes. FIG. 12A shows a spectral reflectance change amount 153 at each incident angle in the case of p-polarized light when the incident angle α [deg] is changed, and FIG. 12B shows a spectral reflectance change amount 154 at each incident angle in the case of s-polarized light when the incident angle α [deg] is changed. As shown in FIG. 12A, in the case of the p-polarized light, the spectral reflectance change amount 153 decreases near an incident angle 50°, and again increases as the incident angle increases. As shown in FIG. 12B, in the case of the s-polarized light, the spectral reflectance change amount 154 uniformly increases to an increase in incident angle.

When the spectral reflectance change amount 153 in the case of the p-polarized light shown in FIG. 12A is compared with the spectral reflectance change amount 133 before track groove embedding in the case of the p-polarized light shown in FIG. 8A, they are the substantially same, and when the spectral reflectance change amount 154 in the case of the s-polarized light shown in FIG. 12B is compared with the spectral reflectance change amount 134 before track groove embedding in the case of the s-polarized light shown in FIG. 8B, the change amount increases as compared with the spectral reflectance change amount 134, and it is known that the sensitivity of detecting the pattern shape does not decrease due to embedding the non-magnetic layer 121 in the track groove and the protective film 122. The reason for this is that a refractive index difference in a pattern boundary portion can be increased by embedding to the track groove 115 and the detecting sensitivity does not decrease.

As described above, also in the third embodiment where the object to be inspected is the discrete track medium 120, similarly to the second embodiment, an abnormal change in pattern shape can be detected with high sensitivity by selecting the polarization direction even in the case of the specimen 1 provided with the track groove embedding and the protective film. Therefore, in the case where the object to be inspected is a product medium, since the detecting sensitivity is not decreased due to embedding to the track groove, it is preferable to inspect the pattern shape in the third embodiment 120 after the non-magnetic layer is embedded in the track groove to perform planarization, and the protective film is formed, because the abnormality in the pattern shape after the second embodiment 110 can be inspected.

Although a lubricating layer is formed after a protective film in an actual product, even after the lubricating layer is formed, similarly an abnormal change in the pattern shape can be inspected.

Fourth Embodiment

Figure 13:
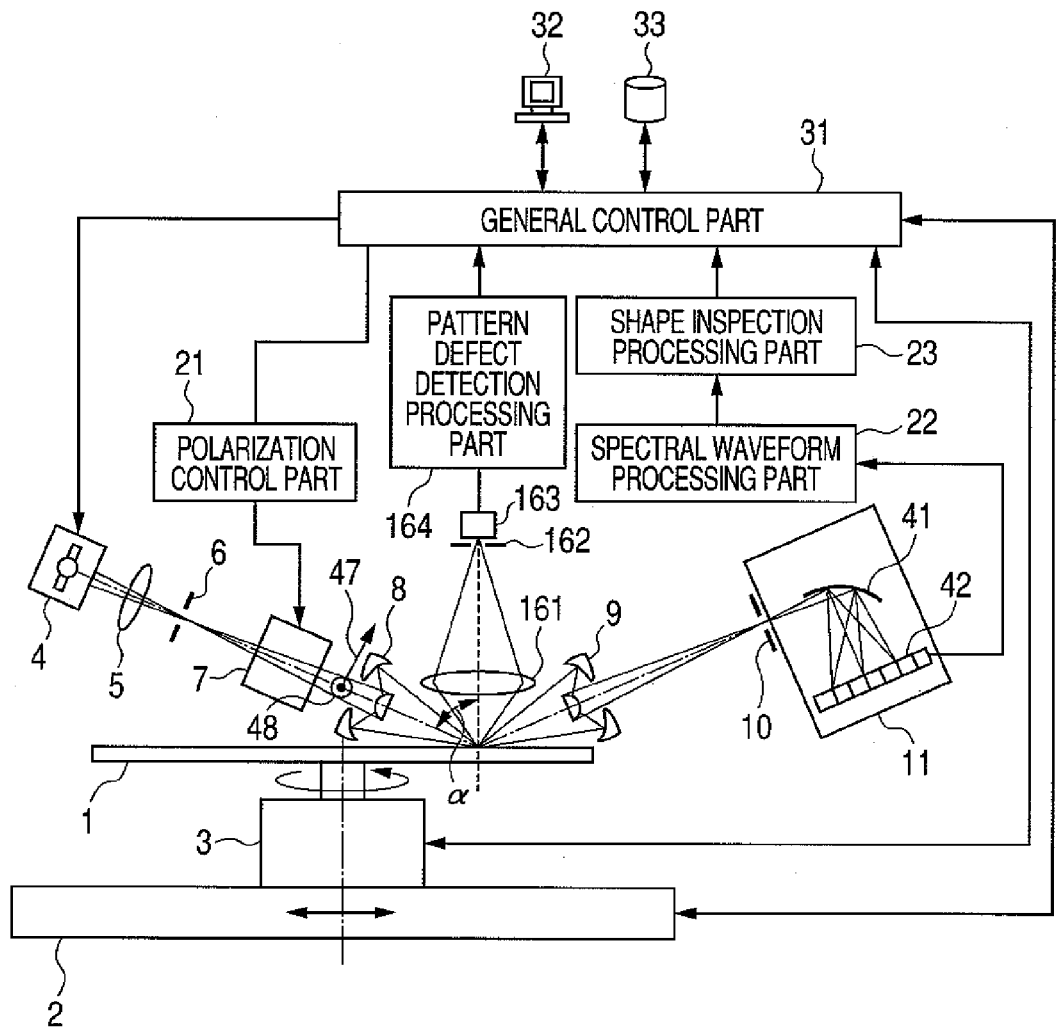
FIG. 13 is a schematic block diagram showing a fourth embodiment of a pattern shape inspection apparatus.

A fourth embodiment of a pattern shape inspection apparatus in accordance with the invention will now be described using FIG. 13. This fourth embodiment is different from the first to third embodiments in that the apparatus further includes a defect detecting system (a defect detecting unit) capable of detecting a defect such as dust particles on a patterned medium, thereby simultaneously performing abnormal detection and defect defection on the pattern shape in the patterned medium. In the configuration of the fourth embodiment, defect detecting systems (defect detecting units) 161 to 164 are added to the optical systems in the first to third embodiments, and the other components outside of the defect detecting system are the same as those of the first to third embodiments. The defect detecting system (the defect detecting unit, as shown in FIG. 13, includes: a scattered light detecting optical system constituted by a condenser lens 161 for condensing upward scattered light from a defect such as dust particles, a diaphragm 162 for shielding stray light or the like and a photo detector 163 for detecting upward scattered light: and a defect detection processing part 164 for detecting a defect such as dust particles from an output signal from the photo detector 163.

The operation of the fourth embodiment will now be described. As an object to be inspected (a specimen 1), similarly to the first embodiment, the stamper 101 for the discrete track medium shown in FIG. 2 is taken. The specimen 1 is held on a θ stage 2, rotated, and also moved in one direction on an X stage 3. Illuminating light of a wide band (multi-wavelength) including far ultraviolet (DUV) light is emitted from a wide band light source 4, and the emitted illuminating light is condensed on a field stop 6 by a condenser lens 5. An image of the field stop 6 is formed on the specimen at an incident angle α by an illuminating lens 8 to form a detecting visual field. At that time, the polarization direction (p-polarized light 47, s-polarized light 48) of illuminating light is determined by a crystal polarizer 7. The polarization direction of illuminating light is previously obtained from conditions for detecting abnormality of a pattern shape of an object to be inspected with high sensitivity, and stored in a database 33.

Therefore, a general control part 31 gives a command for the polarization direction of illuminating light suitable for an object to be inspected, which is stored in the database 33, to a polarization control part 21, and the polarization control part 21 controls the rotation of the crystal polarizer 7 to select the polarization direction of illuminating light to be suitable for the object to be inspected. The zero-order reflected light (regular reflection light) obtained from the detecting visual field of the object to be inspected (the specimen 1) is condensed by an objective lens 9, and imaged on a diaphragm 10. Further, the reflected light form the back of the specimen 1 is shielded by the diaphragm 10, and the detecting light (zero-order reflected light) transmitted through the diaphragm 10 reaches a spectroscope 11 to obtain a spectral waveform. After this, the shape of a recessed and projecting pattern of the object to be inspected is measured and inspected according to the method described in the first embodiment.

A defect detecting system in the fourth embodiment will now be described. Higher-order reflection diffracted light outside of the zero-order of the incident light does not appear because the pattern pitch of the discrete track medium is fine as much as tens of nanometers. When the pattern is made with good accuracy, there is little scattered light toward the upside of the detecting surface to the incident light. On the other hand, when there is a defect such as dust particles or a scratch on the stamper 101, upward scattered light is generated from the defect such as dust particles. The upward scattered light generated from the defect such as dust particles is condensed by the condenser lens 161, and detected by the photo detector 163. As the condenser lens 161 has a larger NA (Numerical Aperture), the higher its detecting sensitivity for the defect such as the dust particles becomes, so a lens with a high NA above 0.4 is used.

In the upward scattered light condensed by the condenser lens 161, the scattered light outside of a detected portion is shielded by the diaphragm 162, and the upward scattered light transmitted through the diaphragm 162 is detected by the photo detector 163. As the photo detector 163, for example, an optoelectronic multiplier tube is used. The intensity of scattered light detected by the photo detector 163 is converted to an electric signal, and the defect such as dust particles is detected in the defect detecting processing part 164. A scattered light intensity signal detected by the photo detector 163 is as shown in FIG. 14.

Figure 14:
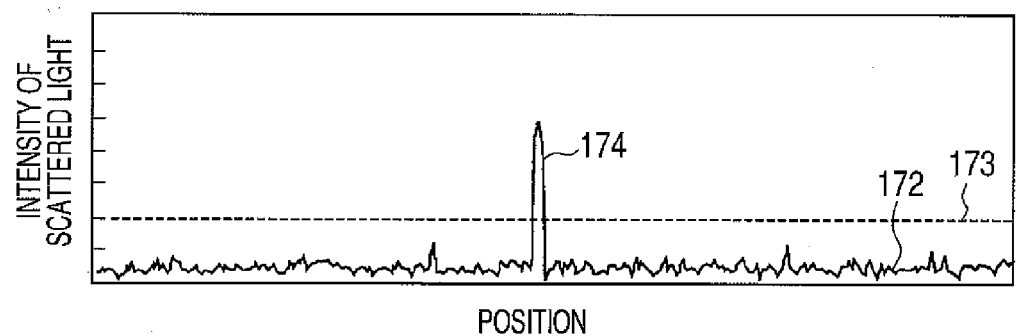
FIG. 14 is a diagram showing a scattered light intensity signal detected by a defect detecting system (a defect detecting unit) shown in FIG. 13.

FIG. 14 shows a scattered light intensity signal 172 in each detecting position with the passage of time depending on θ rotation of the specimen 1. When there is a defect such as dust particles, the scattered light intensity is increased, so the presence 174 of a defect such as dust particles can be detected by previously setting a threshold 173 in the defect detection processing part 164. Therefore, when a defect such as dust particles is detected in the defect detection processing part 164, the general control part 31 records the detecting position in the database 33, and displays it on the input/output terminal 32. When the scattered light is detected in the upper part, generally the detecting sensitivity for the defect such as dust particles differs with the polarization direction of the illuminating light. When the defect such as dust particles is large, the s-polarized light has higher detecting sensitivity, and when it is small, the p-polarized light has higher detecting sensitivity. Therefore, concerning each polarization direction, the detecting sensitivity is measured beforehand, and stored in the database 33, for example. Thus, the defect detection processing part 164 may know the size of a defect such as dust particles from the scattered light detecting intensity by changing the threshold 173 depending on the polarization direction commanded to the polarization control part 21 obtained from the general control part 31.

According to the fourth embodiment, as described above, detection on abnormality in the pattern shape and detection on defect can be simultaneously performed for the stamper 101. As to the object to be inspected (the specimen 1), the inspection is similarly applicable to the discrete track media 110, 120 which are the second and third embodiments in addition to the stamper 101, which is the first embodiment.

Fifth Embodiment

Figure 15:
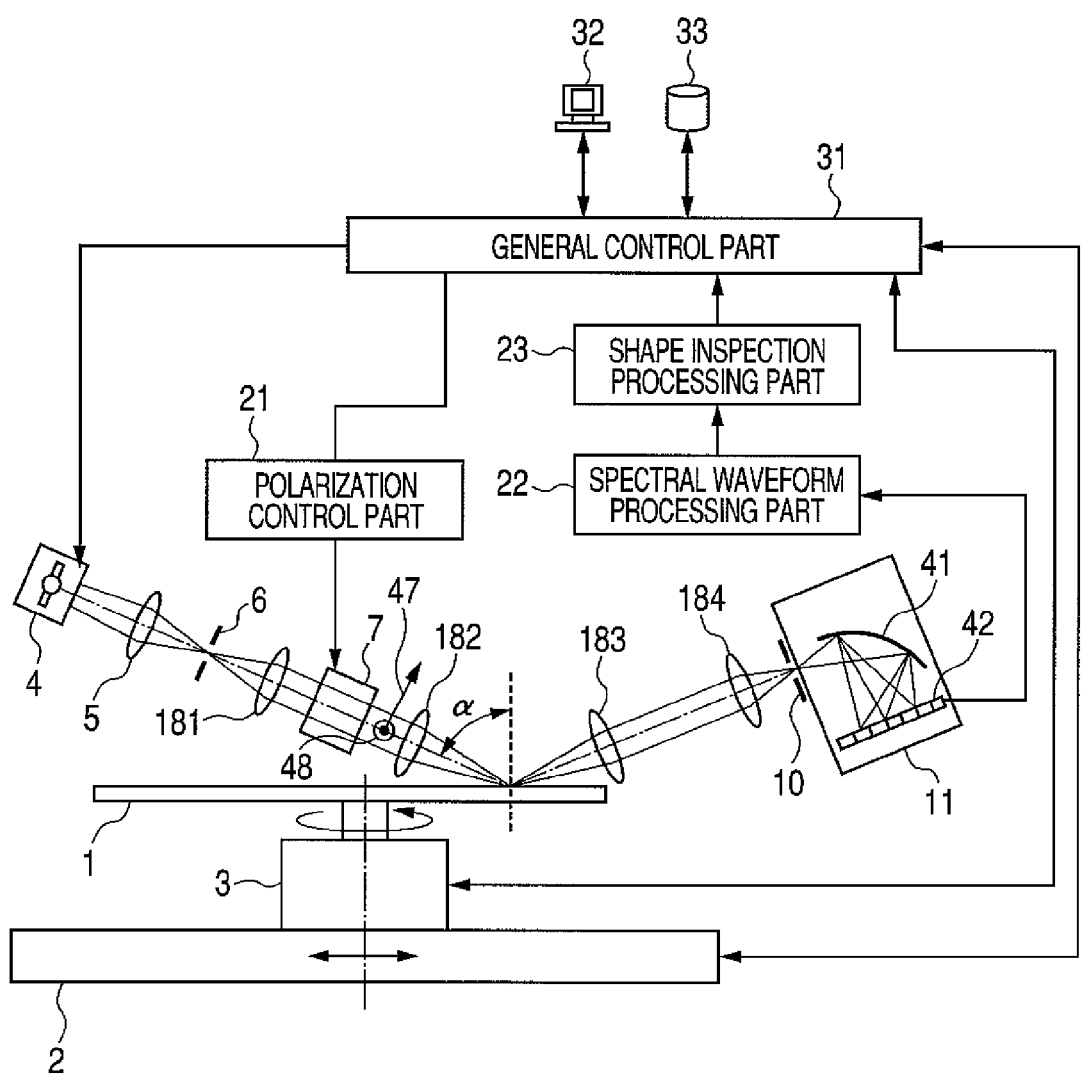
FIG. 15 is a schematic block diagram showing a fifth embodiment of a pattern shape inspection apparatus.

A fifth embodiment of a pattern shape inspection apparatus in accordance with the invention will now be described using FIG. 15. This fifth embodiment is different from the first to fourth embodiments in that the reflection type illuminating lens 8 is replaced with a refraction type lens 181 and an illuminating lens 182, and the reflection type objective lens 9 is replaced with a refraction type objective lens 183 and an imaging lens 184, and the other components are the same as those of the first embodiment shown in FIG. 1 and those of the fourth embodiment shown in FIG. 13. Although the reflection type lens can reduce chromatic aberration in a far ultraviolet region, structurally a mirror is provided on the optical axis, so that during illumination, there is no ray component in the direction of the optical axis, and in detection, no ray in the direction of the optical axis can be detected.

On the other hand, the spectral waveform largely changes depending on its incident angle α. In the case of using the reflection type lens, when the illuminating system and the detecting system are vertical to the specimen, the influence of the incident angle is symmetrical about the optical axis. As in the first to fifth embodiments, however, when the illuminating system is slant incidence and the detecting system is oblique detection, the influence of the incident angle α is asymmetrical about the optical axis so that there is the possibility of causing a large error in detecting a shape change according to the spectral waveform. In the fifth embodiment, a refraction type lens is used instead of the reflection type lens. In the case of the refraction type lens, it is difficult to correct aberration for the wavelength in a wide range, so the refraction type lens whose chromatic aberration is corrected in a comparatively narrow wavelength range is used. In the case of a small pattern, since the detecting sensitivity is higher at the short wavelength side, a lens whose aberration in ultraviolet and far ultraviolet rays is used.

In the operation of the fifth embodiment, similarly to the first to fourth embodiments, illuminating light is applied to the specimen 1 through the refraction type lens 181 and the illuminating lens 182, zero-order reflected light from the specimen 1 is detected through the refraction type objective lens 183 and the imaging lens 184 to obtain a spectral waveform by the spectroscope 11, and a pattern shape is measured from the spectral reflectance waveform obtained in the shape inspecting processing part 23 to inspect an abnormal change.

At this time, since the refraction type objective lens 183 and the imaging lens 184 can detect rays in the direction of the optical axis, the asymmetrical influence of the incident angle on the optical axis is decreased to reduce an error in detecting a shape change according to the spectral waveform. When the chromatic aberration of the refraction type objective lens 183 and the imaging lens 184 can be reduced to a certain extent, the occurrence of blur due to wavelength in the linear photo detector 11 caused by the diffraction grating 41 of the spectroscope 11 is decreased to obtain a high-accuracy spectral waveform.

According to the first to fifth embodiments, as described above, in forming the pattern of the magnetic record medium formed of a patterned medium or a bit patterned medium as an object to be inspected and the pattern of the magnetic record medium by nano-imprint, since the recessed and projecting pattern of the stamper and the recessed and projecting pattern of a master as a die of the stamper are formed in the circumferential direction, a large area or the whole surface of the object to be inspected can be inspected at a high speed by performing the inspection while moving in the circumferential (θ) direction and in the radial (r) direction.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A pattern shape inspection apparatus, comprising:
a moving mechanism on which an object to be inspected where a pattern is formed is placed and which moves the object to be inspected in a radial direction while rotating the object; an irradiating optical system that applies illuminating light of a wide band including far ultraviolet light to the object to be inspected moved in the radial direction while rotating the object by the moving mechanism in a polarized state suitable for the object to be inspected from an oblique direction;
a detecting optical system that detects zero-order reflected light generated from the object to be inspected irradiated by the irradiating optical system; and
a shape inspection unit that inspects a pattern shape formed on the object to be inspected based on a spectral reflectance waveform obtained by dispersing the detected zero-order reflected light.

2. The pattern shape inspection apparatus according to claim 1, further comprising a defect detecting unit that detects a defect on the object to be inspected based on a scattered light intensity signal obtained by detecting scattered light generated from the object to be inspected irradiated by the irradiating optical system.

3. The pattern shape inspection apparatus according to claim 1, wherein the irradiating optical system includes: a wide band light source that emits illuminating light of the wide band; a condenser lens that condenses the illuminating light; a field stop that determines a detecting visual field on the object to be inspected; a polarizing optical element, which controls a polarization direction of the illuminating light to be suitable for the object to be inspected; and an illuminating lens that images the illuminating light whose polarization direction is controlled by the polarizing optical element on the object to be inspected from the oblique direction.

4. The pattern shape inspection apparatus according to claim 1, wherein the detecting optical system includes: an objective lens that images zero-order reflected light generated from the object to be inspected; and a diaphragm that shields stray light.

5. The pattern shape inspection apparatus according to claim 1, wherein the shape inspection means includes a shape inspection processing part that calculates an average error concerning a wavelength between a reference spectral reflectance waveform obtained from a standard object to be inspected and a spectral reflectance waveform of the object to be inspected, and inspects a pattern shape formed on the object to be inspected.

6. The pattern shape inspection apparatus according to claim 1, wherein the object to be inspected is a discrete track medium or a bit patterned medium.

7. The pattern shape inspection apparatus according to claim 1, wherein the object to be inspected is a discrete track medium or a stamper as a die of a bit patterned medium or a master as a die of the stamper.

8. The pattern shape inspection apparatus according to claim 1, wherein when the object to be inspected is a quartz-made stamper, the polarized state of the illuminating light is formed of s-polarized light, and an incident angle in the oblique direction is 70° or more in the irradiating optical system.

9. The pattern shape inspection apparatus according to claim 1, wherein when the object to be inspected is the discrete track medium or the bit patterned medium, the discrete track medium or the bit patterned medium is obtained by embedding a pattern of a magnetic film to achieve planarization, and forming a protective film on the planarized pattern of the magnetic film.

10. A pattern shape inspection method, comprising:
a moving step of placing an object to be inspected where a pattern is formed, and moving the object to be inspected in a radial direction while rotating the object; an irradiating step of applying illuminating light of a wide band including far ultraviolet light to the object to be inspected moved in the radial direction while rotating the object in the moving step in a polarized state suitable for the object to be inspected obliquely from the upside at an incident angle;
a detecting step of detecting zero-order reflected light generated from the object to be inspected irradiated in the irradiating step; and
an inspection step of inspecting a pattern shape formed on the object to be inspected based on a spectral reflectance waveform of the object to be inspected obtained by dispersing the detected zero-order reflected light.

11. The pattern shape inspection method according to claim 10, wherein the method further comprises a defect detecting step of detecting a defect on the object to be inspected based on a scattered light intensity signal obtained by detecting scattered light generated from the object to be inspected irradiated in the irradiating step.

12. The pattern shape inspection method according to claim 10, wherein the object to be inspected is a discrete track medium or a bit patterned medium.

13. The pattern shape inspection method according to claim 10, wherein the object to be inspected is a discrete track medium or a stamper as a die of a bit patterned medium or a master as a die of the stamper.

14. The pattern shape inspection method according to claim 10, wherein when the object to be inspected is a quartz-made stamper, the polarized state of the illuminating light is s-polarized light, and the incident angle obliquely from the upside is 70° or more.

15. The pattern shape inspection method according to claim 12, wherein when the object to be inspected is the discrete track medium or the bit patterned medium, the discrete track medium or the bit patterned medium is obtained by embedding a pattern of a magnetic film to achieve planarization, and forming a protective film on the planarized pattern of the magnetic film.

16. The pattern shape inspection method according to claim 15, wherein the discrete track medium or the bit patterned medium is obtained by forming a lubricating film on the protective film.

17. The pattern shape inspection method according to claim 10, wherein in the inspection step, a mean error concerning a wavelength between a reference spectral reflectance waveform obtained from a standard object to be inspected and a spectral reflectance waveform of the object to be inspected is calculated to inspect a pattern shape formed on the object to be inspected.

* * * * *